US010716555B2

(12) United States Patent
Girard et al.

(10) Patent No.: US 10,716,555 B2
(45) Date of Patent: Jul. 21, 2020

(54) EXPANDER FOR HOLDING APART AN OPENING IN A TISSUE AND METHOD OF OPERATING THE SAME

(71) Applicants: NATIONAL UNIVERSITY OF SINGAPORE, Singapore (SG); SINGAPORE HEALTH SERVICES PTE LTD, Singapore (SG)

(72) Inventors: Michael Julien Alexandre Girard, Singapore (SG); Kian Yu Royston Tan, Singapore (SG); Shamira Asith Perera, Singapore (SG)

(73) Assignees: NATIONAL UNIVERSITY OF SINGAPORE, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 49 days.

(21) Appl. No.: 15/769,735

(22) PCT Filed: Oct. 20, 2016

(86) PCT No.: PCT/SG2016/050510
§ 371 (c)(1),
(2) Date: Apr. 19, 2018

(87) PCT Pub. No.: WO2017/069703
PCT Pub. Date: Apr. 27, 2017

(65) Prior Publication Data
US 2018/0310929 A1     Nov. 1, 2018

Related U.S. Application Data

(60) Provisional application No. 62/243,772, filed on Oct. 20, 2015.

(51) Int. Cl.
*A61B 17/02*     (2006.01)
*A61B 1/32*      (2006.01)
(Continued)

(52) U.S. Cl.
CPC ............ *A61B 17/0231* (2013.01); *A61B 1/32* (2013.01); *A61B 50/30* (2016.02); *A61F 9/007* (2013.01); *A61B 2017/00871* (2013.01)

(58) Field of Classification Search
CPC ....... A61B 17/02; A61B 17/0231; A61B 1/32; A61B 2017/3429; A61B 17/3431
See application file for complete search history.

(56) References Cited

U.S. PATENT DOCUMENTS 2,812,758 A * 11/1957 Blumenschein ... A61B 17/0293
                                                       600/208
4,387,706 A *  6/1983 Glass ................. A61B 17/0231
                                                       600/208
(Continued)

FOREIGN PATENT DOCUMENTS

WO         WO9937215 A1      7/1999
WO       WO2013151685 A1    10/2013
(Continued)

OTHER PUBLICATIONS

Akman, A., et al., "Comparison of Various Pupil Dilatation Methods for Phacoemulsification in Eyes With a Small Pupil Secondary to Pseudoexfoliation", "Ophthalmology", Sep. 2004, p. 6, vol. 111, No. 9, Publisher: American Academy of Ophthalmology.

*Primary Examiner* — Eduardo C Robert
*Assistant Examiner* — Michelle C Eckman
(74) *Attorney, Agent, or Firm* — Hultquist, PLLC; Steven J. Hultquist

(57) ABSTRACT

An expander for widening and holding apart an opening of a tissue. The expander may include a body configured to deform from a compacted state into a pre-determined shape in an expanded state in response to a pre-determined physiological condition the body is exposed to. The body with the
(Continued)

pre-determined shape in the expanded state may be configured to hold apart the opening of the tissue.

13 Claims, 7 Drawing Sheets

(51) Int. Cl.
*A61F 9/007* (2006.01)
*A61B 50/30* (2016.01)
*A61B 17/00* (2006.01)

(56) References Cited

U.S. PATENT DOCUMENTS

| | | | | |
|---|---|---|---|---|
| 4,671,276 A | * | 6/1987 | Reynolds | A61F 2/147 606/166 |
| 4,782,820 A | * | 11/1988 | Woods | A61F 2/14 600/208 |
| 5,267,553 A | * | 12/1993 | Graether | A61B 17/0231 600/236 |
| 5,318,011 A | * | 6/1994 | Federman | B29C 53/086 600/236 |
| 5,322,054 A | * | 6/1994 | Graether | A61B 17/0231 269/303 |
| 5,374,272 A | * | 12/1994 | Arpa | A61B 17/0231 600/236 |
| 5,634,884 A | | 6/1997 | Graether | |
| 6,068,643 A | * | 5/2000 | Milverton | A61B 17/0231 606/107 |
| 6,162,172 A | * | 12/2000 | Cosgrove | A61B 17/0293 600/208 |
| 6,620,098 B1 | * | 9/2003 | Milverton | A61B 17/0231 600/208 |
| 6,675,805 B1 | * | 1/2004 | Graether | A61B 17/0231 128/849 |
| D573,711 S | * | 7/2008 | Johnson | D24/133 |
| 8,323,296 B2 | * | 12/2012 | Malyugin | A61B 17/0231 606/107 |
| 8,496,583 B1 | * | 7/2013 | Reynard | A61B 17/0231 600/235 |
| D735,857 S | * | 8/2015 | Dykes | D24/150 |
| 9,504,459 B1 | * | 11/2016 | Nallakrishnan | A61B 17/0231 |
| 10,130,350 B2 | * | 11/2018 | Akura | A61B 17/0293 |
| 10,307,150 B2 | * | 6/2019 | Kahook | A61B 17/0231 |
| 2003/0092970 A1 | * | 5/2003 | Lee | A61B 17/0231 600/236 |
| 2007/0191941 A1 | * | 8/2007 | Dick | A61F 2/1694 623/4.1 |
| 2008/0228257 A1 | * | 9/2008 | Richter | A61F 2/95 623/1.11 |
| 2012/0289786 A1 | * | 11/2012 | Dusek | A61B 17/0231 600/236 |
| 2013/0096386 A1 | * | 4/2013 | Christensen | A61B 17/0231 600/206 |
| 2013/0131458 A1 | * | 5/2013 | Malyugin | A61B 1/32 600/236 |
| 2013/0267988 A1 | * | 10/2013 | Sussman | A61B 17/0231 606/198 |
| 2014/0107459 A1 | | 4/2014 | Lind et al. | |
| 2014/0221759 A1 | * | 8/2014 | Mackool | A61B 17/0231 600/209 |
| 2014/0276900 A1 | * | 9/2014 | Cote | A61F 9/00736 606/107 |
| 2014/0378773 A1 | * | 12/2014 | Dykes | A61B 17/0293 600/208 |
| 2015/0164685 A1 | * | 6/2015 | Bhattacharjee | A61B 17/0231 606/198 |
| 2015/0366704 A1 | * | 12/2015 | Eippert | A61F 2/14 600/236 |

FOREIGN PATENT DOCUMENTS

WO    WO2014147646 A2    9/2014
WO    WO2014156583 A1    10/2014

* cited by examiner

Single unitary body 100 / 110

FIG. 1 exposing the single unitary body to the pre-determined physiological condition to deform the single unitary body from the compacted state into the pre-determined shape in the expanded state 200 / 202

FIG. 2

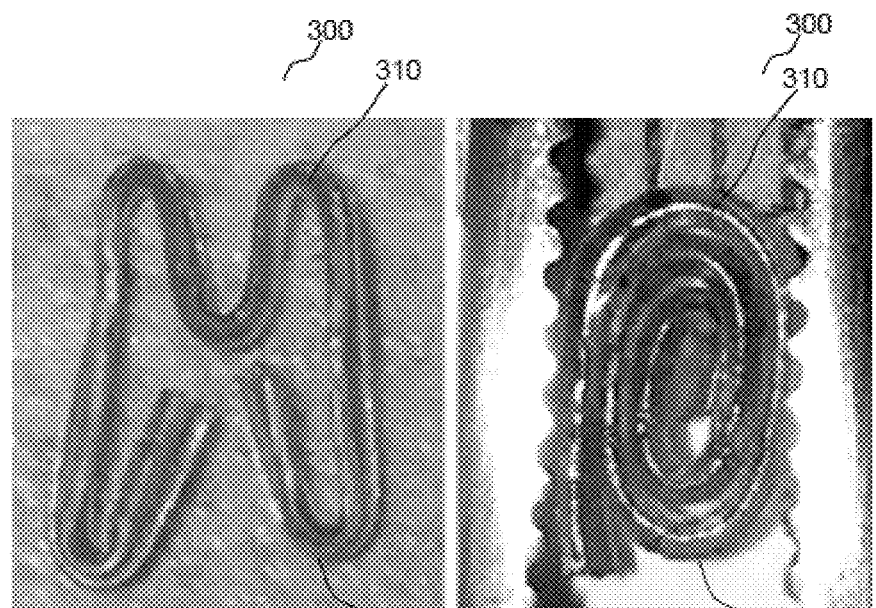
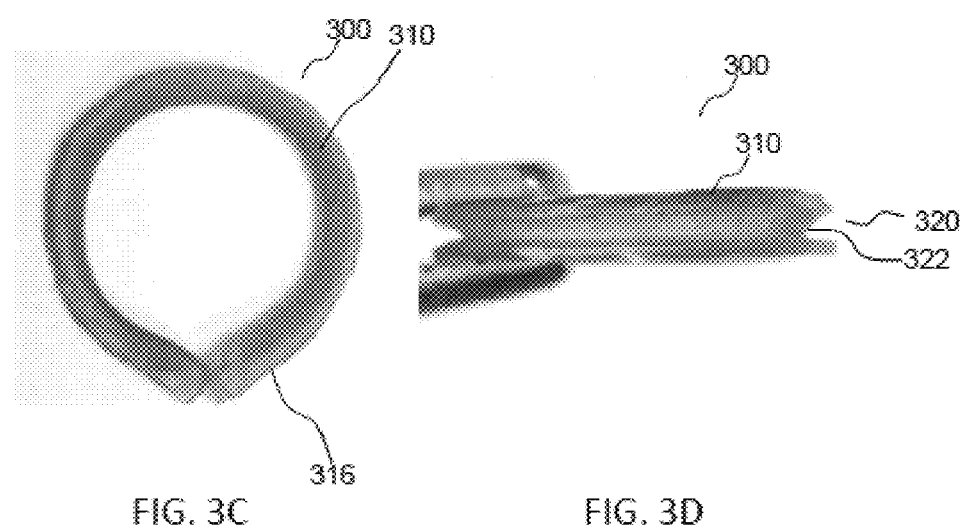

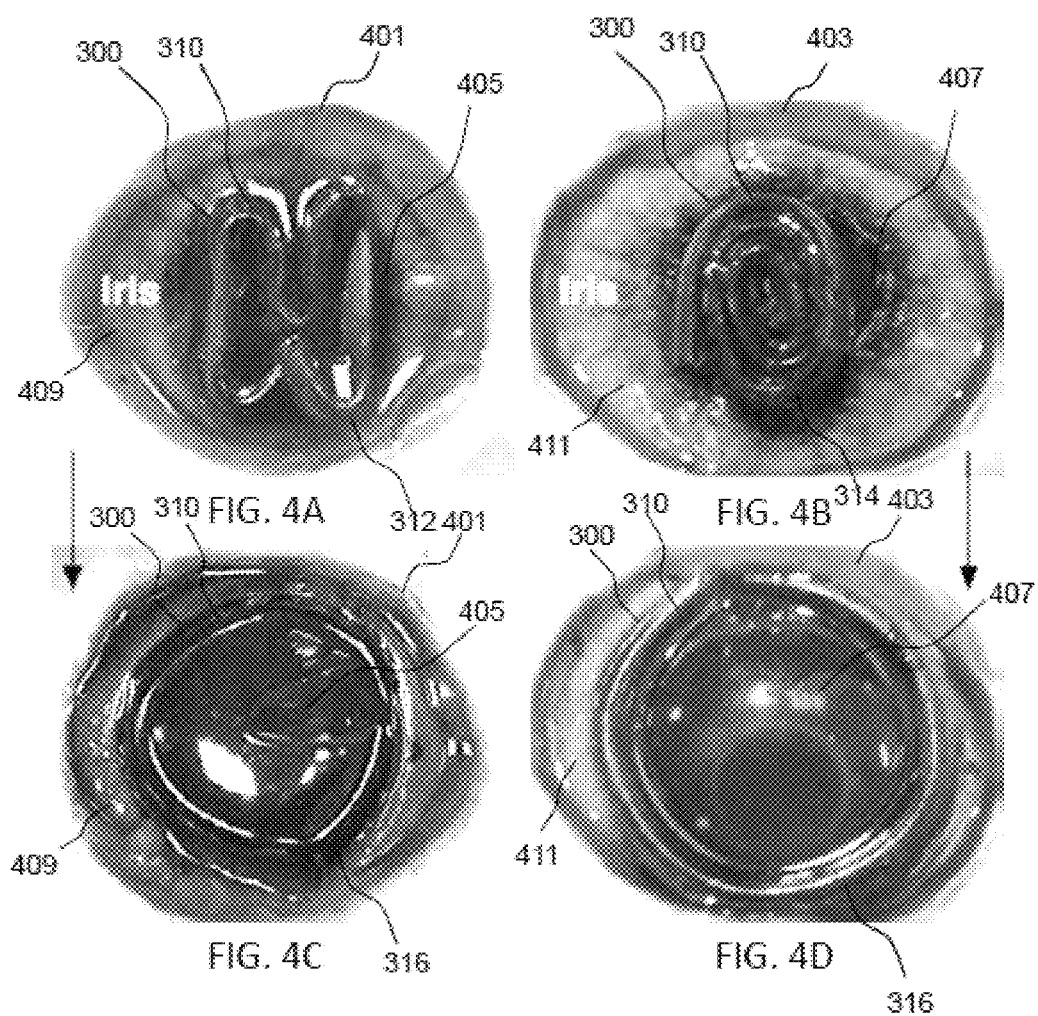

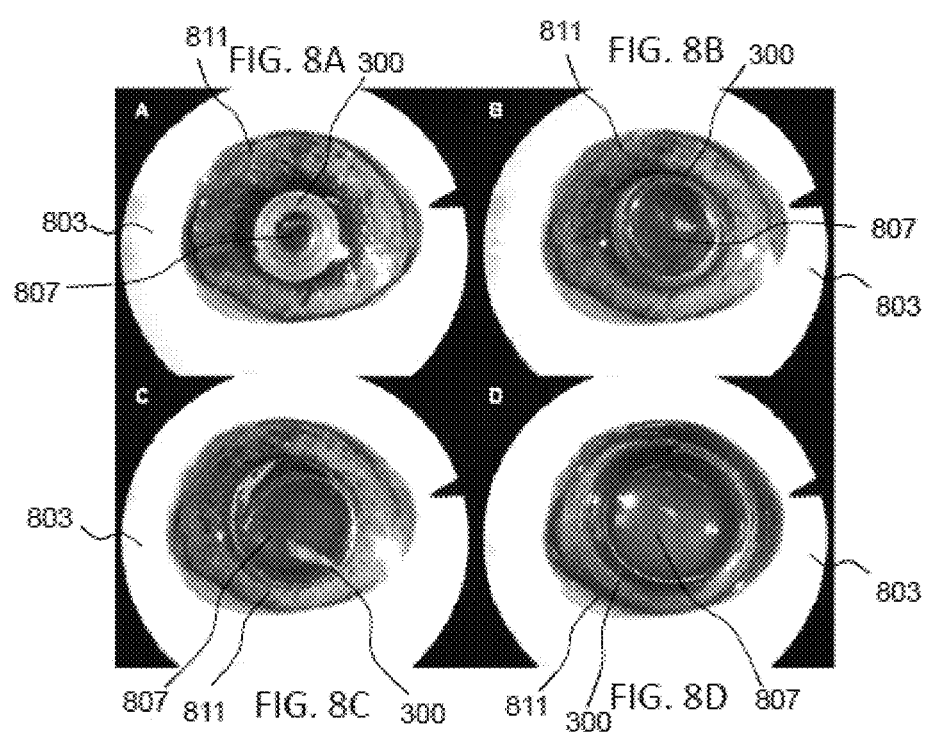

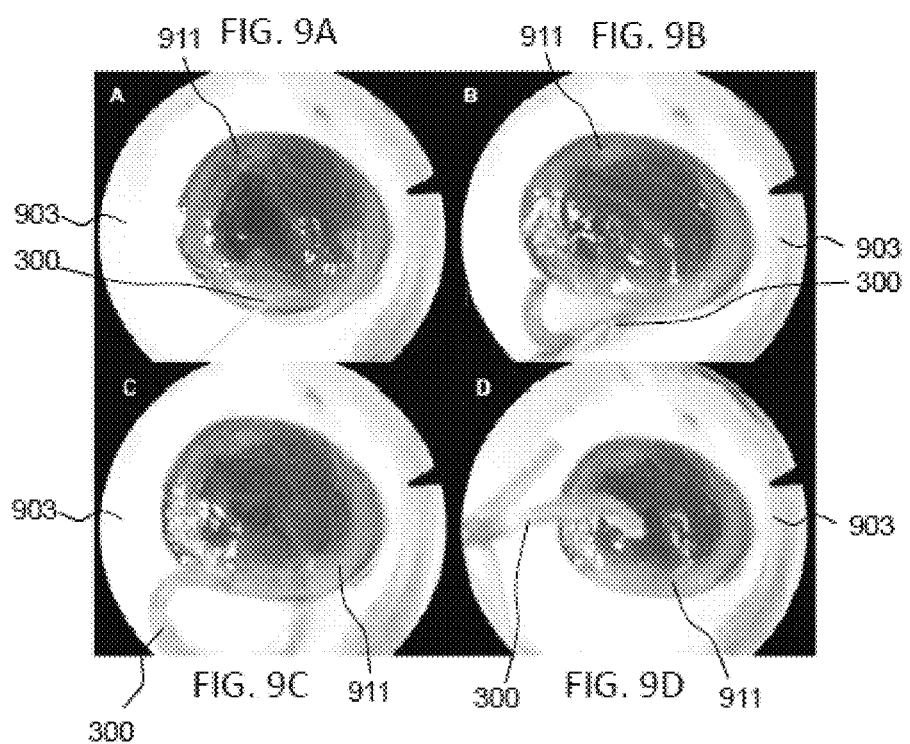

EXPANDER FOR HOLDING APART AN OPENING IN A TISSUE AND METHOD OF OPERATING THE SAME

CROSS-REFERENCE TO RELATED APPLICATIONS

This application is a U.S. national phase under the provisions of 35 U.S.C. § 371 of International Patent Application No. PCT/SG2016/050510 filed Oct. 20, 2016, which in turn claims priority of U.S. Patent Application No. 62/243,772 filed Oct. 20, 2015. The disclosures of such international patent application and U.S. provisional patent application are hereby incorporated herein by reference in their respective entireties, for all purposes.

TECHNICAL FIELD

Embodiments relate generally to an expander for holding apart an opening in a tissue and a method of operating the expander.

BACKGROUND

Cataract is the clouding of the eye's natural lens and commonly results in blindness. In Singapore alone, cataract affects more than 80% of people aged 60 and above. As life expectancy continues to increase, it is expected that every individual will at some point of his life undergo cataract surgery. Today, cataract surgery is in fact the most common surgery across all fields of medicine with an estimated 20,000,000 surgeries performed each year worldwide. Cataract surgery involves removing the 'cloudy' lens and replacing it with an optically clear implant, referred to as an intraocular lens (IOL) implant.

To ensure the success of cataract surgery, there is a strong clinical need for a clear and unobstructed view of the lens for the surgeon. The lens is covered in part by the iris—the muscle tissue that is responsible for opening the pupil. In other words, for cataract surgery to succeed, the ophthalmic surgeon requires an adequately large pupil opening.

Several clinical options are already available to enlarge the pupil during cataract surgery. The most common approach is pharmacological, and involves using dilating eye drops. Eye drops, however, are controlled substances, which can cause side effects such as allergic reactions and conjunctival injection. Eye drops have been found to be ineffective, either through a partial or total lack of dilation, in a substantial number of patients.

An alternative approach to enlarge pupils is mechanical, and relies on temporarily inserting a mechanical device (iris/pupil expander) into the front chamber of the eye (anterior chamber) to apply a mechanical force to the iris, thus enlarging the pupil.

Iris (or pupil) expanders have been available since the 1980s. Earlier iterations were made from flexible resilient materials like silicone, directly inserted into the eye via a corneal incision. The ring pushes against one portion of the pupil and is then slotted in to the remainder of the iris to create mechanical circular dilation of the pupil. The Iris Retractor (U.S. Pat. No. 4,387,706), developed by Robert M. Glass, was one such example. However, an issue with using such pupil expanders is that large corneal incisions are required which may lead to prolonged post-operative recovery.

To temporarily stretch the pupil, the surgeon can use instruments such as a Sinskey hook, or a Beehler pupil dilator. For these hooks, they are introduced through two incisions in the cornea and engage the iris at opposite ends. The hooks are then pulled apart in opposite directions to cause micro tears in the iris sphincter that result in a slightly enlarged pupil size. But the use of these hooks can be counter-productive if done incorrectly and may cause iris prolapse out of the incision by rendering it too floppy.

There are other drawbacks to mechanical stretching and sphincter cuts. Firstly, the micro tears caused to the iris sphincter muscle are irreversible. Although, usually asymptomatic, in some cases they could lead to postoperative bleeding, pigment dispersion, atonic pupil shape and minimal dilation. For Sinskey hooks, the mean pupil size achieved is 4.9±0.7 mm while for Beehler pupil dilators, the mean pupil size achieved is 5.5±0.8 mm. The relatively small dilation size achieved may not justify the possible permanent damage to the iris.

One of the oldest and most popular iris expanders are iris hooks. Four iris hooks evenly spaced 90° apart from each other resulting in a diamond shaped opening. This method is relatively simple to execute, but adds on a mean time of 297±51 seconds for insertion to the surgery (Akman et al, 2004) and sometimes lifts the pupil edge up, making surgery more challenging. Having four additional incisions also increases the chances of infection and post-operative inflammatory response. Even so, the maximum pupil dilation achieved was reported to be only a 5.5 mm diameter circle. Iris hooks can also damage the pupillary margin, which results in prolonged abnormal dilation. The unique advantage is their flexibility in being able to also hook into the capsular bag, if needed, to stabilize this in cases of zonulysis and the crystalline lens is tipping downwards.

Recent designs of pupil expanders have favored slimmer and flexible rings e.g. the Malyugin Ring, whose four corner helical loops engage the iris. Similarly the Oasis Ring, substitutes pockets for loops. However, the ring can flip out of plane and damage the cornea. The iris margin can also become temporarily caught by the helical loops and some force is required to pull out the ring, and it can be traumatic to the iris margin to insert through a small pupil and may interfere with surgery becoming dislodged during the phacoemulsification. Further, the downside of such rings is that insertion through a very small 3 mm pupil is impossible and such ring can only be used to expand a moderately dilated pupil to a larger one. The Bhattacharjee Ring is an alternative that has six points of capture, but is fiddly to insert and remove. The Assia pupil expander is a new, metallic, crude square pupil expander that is not widely used but requires additional moderate size incisions.

The Perfect Pupil is a flexible polyurethane iris expansion ring. It has a luxurious internal diameter of 7 mm. The Perfect Pupil is first inserted fully into the anterior chamber of the eye so that it is resting on the iris. The surgeon then engages the primary fenestration before proceeding around. It will typically take an average of 4 minutes for insertion and withdrawal. In addition, the attachment of the fenestrations can cause iris chafing to occur. The Perfect Pupil is also not fully circular in configuration, but rather is a configured into a 270°-320° circle sector.

Older pupil expansion rings include the Morcher 5S Pupil and the disposable silicone Eagle Vision Graether Ring both of which are threaded along the pupillary margin using an injector. However, these rings are difficult to position if the anterior chamber is shallow or the pupil is less than 4 mm wide.

As can be seen, most of these pupil expanders are crude and poorly designed. Most of these pupil expanders are also difficult to insert, deploy and retract into a truly small diameter pupil and if so, do not manage to dilate the pupil very dramatically. Furthermore, some of these pupil expanders require corneal incisions for insertion. Some of these pupil expanders deform the pupil to a square-shaped opening, which is unnatural. In addition, some of these pupil expanders can result in considerable damage and trauma to the iris, thus highly impacting its functionality. As such, they cannot be considered as true substitutes for pupil dilation with drops prior to surgery or prior to Femtosecond Laser-Assisted Cataract Surgery (FLACS).

Accordingly, example embodiments seek to provide an expander for widening and holding apart an opening in a tissue and a method of operating the expander that addresses at least some of the issues identified above.

SUMMARY

According to various embodiments, there is provided an expander for widening and holding apart an opening of a tissue. The expander may include a body configured to deform from a compacted state into a pre-determined shape in an expanded state in response to a pre-determined physiological condition the body is exposed to. The body with the pre-determined shape in the expanded state may be configured to hold apart the opening of the tissue.

According to various embodiments, there is provided a method of operating the expander as described herein. The method may include exposing the body to the pre-determined physiological condition to deform the body from the compacted state into the pre-determined shape in the expanded state.

According to various embodiments, there is provided a method of manufacturing the expander as described herein. The method may include providing a body configured to deform from a compacted state into a pre-determined shape in an expanded state in response to a pre-determined physiological condition the body is exposed to, wherein the body with the pre-determined shape in the expanded state may be configured to hold apart the opening of the tissue.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIG. 1 shows a schematic diagram of an expander for widening and holding apart an opening of a tissue according to various embodiments;

FIG. 2 shows a method of operating the expander of FIG. 1 according to various embodiments;

FIGS. 3A and 3B show various examples of an expander in a compacted state according to various embodiments;

FIG. 3C shows an example of the expander of FIGS. 3A and 3B in the expanded state according to various embodiments;

FIG. 3D shows a side view of the expander in the expanded state of FIG. 3C according to various embodiments;

FIGS. 4A and 4B show the respective examples of the expander in the compacted state of FIGS. 3A and 3B being inserted into respective eyes according to various embodiments;

FIGS. 4C and 4D show the respective expander of FIGS. 4A and 4B expanded to a circular shape to enlarge the pupil of the respective eye according to various embodiments;

FIGS. 8A to 8D illustrate the expansion of the expander of FIG. 3 to engage the iris of an eye according to various embodiments; and FIGS. 9A to 9D illustrate the removal of the expander from an eye according to various embodiments.

DETAILED DESCRIPTION

Figure 5:
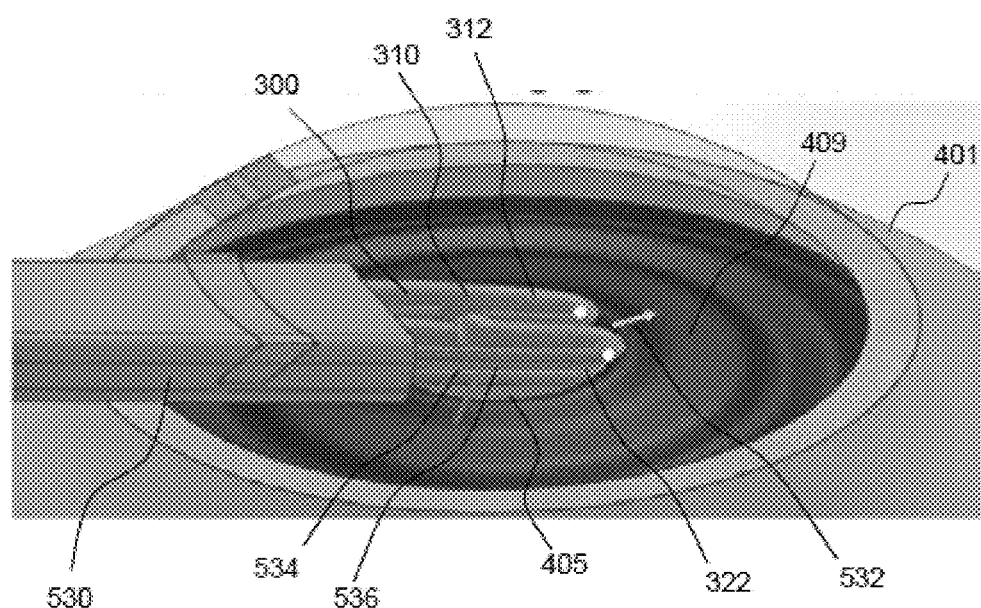
FIG. 5 illustrate the insertion of the expander of FIG. 3A into the eye using an injector according to various embodiments.

Embodiments described below in context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure, whether in use or otherwise. In addition, the singular terms "a", "an", and "the" include plural referents unless context clearly indicates otherwise. Similarly, the word "or" is intended to include "and" unless the context clearly indicates otherwise.

FIG. 1 shows a schematic diagram of an expander 100 for widening and holding apart an opening of a tissue according to various embodiments. According to various embodiments, the tissue may be an iris of an eye, and the opening in the tissue may be a pupil of the eye. It is also understood that the opening may be a cut or formed from one or more cuts in any body tissue. The opening of the tissue may also be a passage in a blood vessel.

According to various embodiments, the expander 100 may include a body 110. The body 110 may be a line structure, or a closed loop structure. The body 110 may be a single unitary body. Further, the body 110 may be configured to deform from a compacted state (or an initial state or a relaxed state or a folded state or a stowed state or an original state) into a pre-determined shape in an expanded state (or a stimulated state or a deployed state) in response to a pre-determined physiological condition the body is exposed to. Thus, the body 110 of the expander 100 may be configured such that by exposing or subjecting the body 110 to the pre-determined physiological condition, for example by inserting the body 110 of the expander 100 into the target opening of the target tissue to expose or subject the body 110 of the expander 100 to the conditions of the natural internal milieu of the target tissue, the body 110 of the expander 100 may respond to the stimulation of the physiological condition of the target tissue, or may be triggered by the stimulation, to change or transform the shape or size of the body 110 of the expander 100 into a pre-determined shape in the expanded state. Accordingly, without the stimulation or the trigger of exposing or subjecting the body 110 of the expander 100 to the pre-determined physiological condition, the body 110 of the expander 100 may remain in the compacted state and may not be deformed into the pre-determined shape.

According to various embodiments, deformation of the body 110 of the expander 100 may be reversible. Accordingly, when the body 110 of the expander 100 is no longer exposed or subjected to the pre-determined physiological condition, for example when the body 110 of the expander 100 is removed from the tissue, the body 110 of the expander 100 may revert back to the compacted state from the expanded state.

According to various embodiments, the body 110 of the expander 100 with the pre-determined shape in the expanded state may be configured to hold apart the opening in the tissue. Accordingly, the body 110 of the expander 100 with the pre-determined shape in the expanded state may be configured to be resilient such that the body 110 of the expander 100 may have the natural tendency to maintain the pre-determined shape in the expanded state so as to apply a biasing force against the edge of the tissue forming the opening for holding apart the tissue to maintain the opening.

In other words, various embodiments of the expander 100 may include a structure configured to transform from an original state into a deployed state for holding apart the opening of the tissue. The transformation of the structure may include changing the shape of the structure into a pre-defined shape. Further, the structure may be configured to trigger the transformation as a result of the structure being exposed to a pre-determined physiological condition. Thus, when the structure is placed or put in an environment having the pre-determined physiological condition, the structure may react such that the structure may transform into the pre-defined shape. In the deployed state, the structure with the pre-defined shape may provide the necessary frame for holding apart the opening of the tissue.

According to various embodiments, deformation of the body 110 may be gradual over a period of time of at least one second, or 1 to 10 seconds, or 5 to 15 seconds, or 10 to 20 seconds, or 15 to 25 seconds, or 20 to 30 seconds, or 25 to 35 seconds. Accordingly, the body 110 may deform from the compacted state into the pre-determined shape in the expanded state in response to the pre-determined physiological condition in a progressive and incremental manner. In other words, the deformation may not be sudden or instantaneous, and may not be abrupt. Rather, the deformation may be taking place relatively slowly bit by bit and in small degree of changes. Advantageously, gradual deformation of the body 110 of the expander 100 may prevent injury or damage to the tissue as the expander 100 deforms to widen and hold apart the opening of the tissue. Further, the gradual deformation of the body 110 of the expander 100 may allow the user or surgeon to adjust the position of the body 110 of the expander 100 relative to the opening of the tissue while the body 110 of the expander 100 may be in the process of deforming into the pre-determined shape of the expanded state. Accordingly, the expander 100 may allow ease and convenience of achieving controlled expansion of the opening of a tissue.

According to various embodiments, the expander 100 may include a pouch enclosing the body 110 to maintain the body 110 in the compacted state. The pouch may be configured to be dissolvable or soluble in the tissue to expose the body 110 for deforming from the compacted state to the pre-determined shape in the expanded state. The pouch may include a bag, a sack, a sac or any form of receptacle for containing the body 110. The body 110 may be compressed or folded or squeezed or packed into the pouch so that the body 110 may be in the compacted state. The pouch may be made of a material that may dissolve, disintegrate, or degrade when being expose to the pre-determined physiological condition of the tissue. For example, polyvinyl alcohol has water soluble properties, which when use along with other compounds may be a suitable material for the pouch so as to achieve controlled dissolution when expose to the pre-determined physiological condition of the tissue. Accordingly, when the expander 100 is being inserted into the opening of the tissue, the pouch may dissolve or disintegrate or degrade in response to the pre-determined physiological condition of the tissue such that the body 110 of the expander 100 may be released or exposed from the pouch for deforming into the pre-determined shape in the expanded state.

According to various embodiments, the body 110 of the expander 100 may include a glue or a coating configured to maintain the body 110 in the compacted state and further configured to be dissolvable in the tissue to expose the body 110 for deforming from the compacted state to the pre-determined shape in the expanded state. In the compacted state, the glue or the coating of the body 110 of the expander 100 may provide the necessary rigidity or stiffness to the body 110 to maintain the body 110 in the compacted state. The glue or the coating may be made of a material that may dissolve, disintegrate, or degrade when being exposed to the pre-determined physiological condition of the tissue. Accordingly, when the expander 100 is being inserted into the opening of the tissue, the glue or the coating may dissolve or disintegrate or melt away in response to the pre-determined physiological condition of the tissue such that the glue or the coating may no longer provide the rigidity or stiffness to the body 110 and the body 110 may be released or exposed for deforming into the pre-determined shape in the expanded state.

According to various embodiments, deformation of the body 110 of the expander 100 from the compacted state into the pre-determined shape in the expanded state may cause the widening of the opening of the tissue. Accordingly, the body 110 may be placed in the opening of the tissue when the body 110 is in the compacted state. As the body 110 is stimulated by the physiological condition while in the opening of the tissue, the body 110 may start to deform to form the pre-determined shape. The pre-determined shape may be a shape with a width wider than an original width of the original opening of the tissue. Thus, as the body 110 deforms, the body 110 may push against the edge of the tissue forming the opening. The pushing by the deforming body 110 of the expander 100 may cause the opening of the tissue to widen. When the body 110 is fully deformed to form the pre-determined shape, the widening of the opening of the tissue may be completed and the body 110 of the expander 100 may hold the tissue apart to maintain the enlarged or widen opening.

According to various embodiments, the body 110, in the compacted state, may be in a folded shape. Accordingly, in the compacted state, the body 110 may be pre-worked or pre-formed or pre-set into the folded shape for inserting into the opening of the tissue. In the compacted state, after the body 110 is folded, bent, worked, formed, molded or shaped into the folded shape, the body 110 may remain in the formed desired shape and may not return to its original shape. The desired folded shape may be a shape that is compressed, compacted, condensed or squeezed such that there may not be much space within the folded shape.

According to various embodiments, the folded shape of the body 110 in the compacted state may include a shape with an optimum compactness. According to various embodiments, the folded shape may be a compressed folded shape. Accordingly, by having a folded shape that is compacted, compressed, condensed or squeezed, the body 110 may be easily inserted into the opening of the tissue. For example, when the opening is a pupil of an eye, only a small slit or cut in the cornea may be required to insert the expander 100 that is folded into a shape which is compacted, compressed, condensed or squeezed. Compactness may be measured in terms of the ratio of the area of the desired shape to the area of a circle (which is considered the most compact shape) having the same perimeter. According to various embodiments, the folded shape may have a compactness with a ratio close to 1, for example between 1 to 1.5. Advantageously, the compact shape may allow the expander 100 to be usable in surgeries involving eyes of various dimensions, even including Asian eyes, which tend to be physically smaller in dimension.

According to various embodiments, the folded shape may include a chromosome shape, a M-shape, a zig-zag shape, a spiral shape or a coiled shape. According to various embodiments, the chromosome shape, the M-shape and the zig-zag shape may be compressed or packed such that each link of the M-shape or the zig-zag shape may be closed to or in contact with an adjacent link so as to minimize space in between the links. According to various embodiments, the spiral shape or the coiled shape may be compressed or packed such that the rings of the spiral or the coil may be closed to or in contact with each other so as to minimize space in between the rings.

According to various embodiments, the body 110 of the expander 100, in the expanded state, may be configured to be elastically deformable under an applied force for bending the body, and configured to return to the pre-determined shape upon the removal of the applied force. Accordingly, although the body 110 in the expanded state may have the natural tendency to maintain the pre-determined shape, the body 110 may be configured such that it may still be deformed or bent under the application of a force. This may allow the body 110 of the expander 100 to be deformed or bent in the expanded state such that the body 110 of the expander 100 may be removed from the tissue after it has been introduced into the opening of the tissue. According to various embodiment, a difference between the deformation characteristic of the body 110 of the expander 100 in the expanded state and in the compacted state may be that, in the expanded state, the body 110 may be resilient and may rebound or return to the pre-determined shape after the force is removed. On the other hand, in the compacted state, the body 110 may not return to its original shape after it has been folded and the force for folding the body 110 has been removed.

According to various embodiments, the pre-determined physiological condition may include a temperature, a pressure or a concentration. For example, the temperature may be a temperature inside the opening of the tissue, the pressure may be a fluid pressure inside the opening of the tissue, and the concentration may be a particular fluid concentration or a gaseous concentration inside the opening of the tissue. According to various embodiments, the physiological condition may include a pre-determined temperature, for example a pre-determined body temperature. According to various embodiments, the pre-determined temperature may be a temperature that is higher than a temperature of the expander 100 in the compacted state when stored. For example, the pre-determined temperature may be 27 degrees Celsius and above, or 35 degrees Celsius and above, or any other suitable temperature.

According to various embodiments, the body 110 of the expander 100 may be further configured to deform from the compacted state into the pre-determined shape in the expanded state in response to an external stimulation. The external stimulation may include a thermal source external to the tissue, or a fluid with a pre-determined temperature. For example, a thermal source external to the tissue may be a laser equipment adapted to heat up the tissue or to heat up the expander 100 in the tissue. A fluid with a pre-determined temperature may be warm water that may be used to flush the tissue to heat up the tissue or the expander 100 in the tissue.

According to various embodiments, the pre-determined shape may include an annular circular shape, an annular oval shape, an annular elliptical shape, or a horseshoe shape or any suitable spread-out shape. Accordingly, in such pre-determined shape, the body 110 of the expander 100 may engage the tissue along an entire circumference of the body 110 in the expanded state, or may have a 360 degree contact with the tissue. Further, as the body 110 may be a line structure, it is understood that the pre-determined shape may also include a substantially annular circular shape with a broken connection, a substantially annular oval shape with a broken connection or a substantially annular elliptical shape with a broken connection.

According to various embodiments, a side or a surface of the body 110 of the expander 100, in the expanded state, may be configured to engage the opening of the tissue and the side of the body 110 may be in direct contact with the tissue. The side or the surface of the body 110 may be the outermost exterior surface of the body 110 in the expanded state. Accordingly, the side of the body 110 may be shaped and dimensioned such that the edge of the tissue may be received by the side of the body 110. When the pre-determined shape is the annular circular shape, the annular oval shape, the elliptical shape or the horseshoe shape, the side of the body 110 may be the outer or the exterior circumferential surface of the pre-determined shape of the body 110 in the expanded state. In this configuration, the body 110 of the expander 100 in the expanded state may apply a uniform force and pressure on the edge of the tissue forming the opening, and minimise tears and damage to the tissue. The body 110 of the expander 100 in the expanded state may also have a 360 degree contact or engagement with the opening of the tissue. In this way, the body 110 of the expander 100 may also function as a shield to the tissue to prevent damage by surgical tools used by the surgeon during surgery. Accordingly, the body 110 may include a continuous recess along the circumferential surface of the pre-determined shape of the body 110 in the expanded state. The continuous recess may encircle the body 110 in the expanded state. Thus, the edge of the tissue forming the opening may be engaged and received in the continuous recess. When the opening of the tissue is a pupil of an eye, the recess on the circumferential surface of the body 110 in the expanded state may receive and engage with the iris of the eye.

According to various embodiments, a portion of the side or the circumferential surface of the body 110, in the compacted state, may be configured to engage a holder of an injector. The injector may include a holder movable relative to an injector body. Accordingly, the holder may be extended from the injector body and may be retracted into the injector body. To place the expander 100 into the opening of a tissue, the expander 100 in the compacted state may be held by the injector such that a portion of the side of the body 110 in the compacted state may be engaged to the extended holder of the injector for supporting the expander 100 on the holder of the injector. The operator may then operate or handle the injector to position the expander 100 into the opening of the tissue. When the expander 100 is at the desired position within the opening of the tissue, the operator may retract the holder of the injector such that the expander 100 may be released from the injector for placing at the desired position.

According to various embodiments, the holder may include a pair of rod-like structures. Accordingly, the recess in the side or the circumferential surface of the body 110 may receive and engage with the pair of rod-like structures such that the expander 100 may be supported by the holder of the injector.

According to various embodiments, the body 110 may include a C-shaped cross section, a U-shaped cross section or a horseshoe-shaped cross section. Accordingly, the cavity of the C-shaped cross section, the U-shaped cross section or the horseshoe-shaped cross section may be oriented to form the recess of the side or the circumferential surface of the body 110 that may be configured to engage the opening of the tissue when the body 110 is in the expanded state.

According to various embodiments, the body 110 of the expander 100 may be made of biocompatible materials. The body 110 may be also made of shape-memory polymer. Accordingly, the body 110 may be made of biocompatible shape-memory material. According to various embodiments, the body 110 of the expander 100 may be made of a shape memory polymer. An example of the shape memory polymer may be polyurethane having a soft segment and a hard segment. The soft segment may include materials such as Polycaprolactone (PCL). The hard segment may include materials such as 4,4'-diphenylmethane diidocyanate (MDI) and 1,4-butanediol (BDO). According to various embodiments, the body 110 of the expander 100 may be made of shape memory alloy. An example of the shape memory alloy may be nitinol. Accordingly, the shape memory materials may have a physically deformable shape that may be capable of returning to a pre-set or pre-determined shape upon exposure to a pre-determined stimulation. According to various embodiments, the body 110 of the expander 100 may be made of hyperelastic/visco-hyperelastic material that may be accompanied with a gluing agent for controlled release. Example of hyperelastic/visco-hyperelastic material may include, but not limited to, silicone based rubbers, polydimethylsiloxane (PDMS), poly(methyl methacrylate (PMMA), polyvinylchloride (PVC), polyvinyl alcohol (PVA), etc.

FIG. 2 shows a method 200 of operating the expander 100 of FIG. 1 according to various embodiments. The method may include at 202, exposing the body to the pre-determined physiological condition to deform the body from the compacted state into the pre-determined shape in the expanded state.

According to various embodiments, the method may further include holding the body in the compacted state with a holder of an injector. Further, the holder of the injector may include a pair of rod-like structures.

According to various embodiments, there may be provided a method of manufacturing the expander 100 of FIG. 1 according to various embodiments. The method may include providing a body configured to deform from a compacted state into a pre-determined shape in an expanded state in response to a pre-determined physiological condition the body is exposed to, wherein the body with the pre-determined shape in the expanded state may be configured to hold apart the opening of the tissue.

According to various embodiments, there is provided an expander for widening and holding apart an opening of a tissue. For example, various embodiments have provided pupil expanders (or iris expanders) suitable for used in ophthalmological surgeries with the purpose of engaging the iris and applying mechanical forces to reveal a larger pupil. The purpose of the pupil expanders may be to increase the diameter of the pupil for surgical procedures such as (but not limited to) cataract surgeries. According to various embodiments, the expander may apply a required mechanical force to the iris for increasing the diameter of the pupil when expose to an increase in energy (for example increase in temperature).

FIGS. 3A and 3B show various examples of an expander 300 in the compacted state according to various embodiments. The expander 300 may be suitable for used in ophthalmological surgeries, in particular, for enlarging a pupil of an eye. According to various embodiments, the expander 300 may include a body 310. As shown, the body 310 may be a line structure and may be a single unitary body. The body 310 may be made of a type of 'smart' material that may be folded due to its flexibility in the compacted state. The 'smart' material may be a type of shape-memory polymer. As shown, the expander 300 in the compacted state may be folded into an M shape 312 in FIG. 3A, or a spiral shape 314 in FIG. 3B. The expander 300 may be folded for easy insertion into the eye. According to various embodiments, the expander 300 may be foldable to any desired folded shape with an optimum compactness such that it may be inserted into the eye via a small incision, for example an incision of about 2 mm by 1 mm. FIG. 4A shows the expander 300 folded into an M shape 312 and inserted into an eye 401. FIG. 4B shows the expander 300 folded into a spiral shape 314 and inserted into an eye 403. As shown, the expander 300 may be in a folded shape such that the expander 300 may be sufficiently compact to be placed inside the pupil 405, 407, which is normally 2-3 mm in diameter when undilated, of the respective eyes 401, 403.

To expand or enlarge the pupil, the body 310 of the expander 300 may deform into a pre-programmed or pre-determined shape, for example a circular ring 316 as shown in FIG. 3C, upon exposure to a physiological condition of the eye, for example a pre-determined temperature of the eye. The pre-determined temperature may be a temperature that is higher than a temperature of the expander 300 in the compacted state when stored. An example of the pre-determined temperature may be that of the eye anterior chamber, or may be a temperature of 27 degree Celsius, or may be a temperature of 35 degree Celsius, or any other suitable temperature.

Accordingly, the body 310 of the expander 300 may be configured to deform from the compacted state into a pre-determined shape in an expanded state in response to the pre-determined physiological condition the body 310 is being exposed to. The deformation of the body 310 from the compacted state into the pre-determined shape in the expanded state may cause the widening of the pupil 405, 407 of the eye 401, 403 to enlarge the size of the pupil 405, 407 by applying a force to push back the iris 409, 411 of the eye 401, 403 as the body 310 deforms to form the circular ring 316 as shown in FIG. 3C. For example, the expander 300 after deforming into the circular ring 316 in the expanded state may enlarge the pupil 405, 407 to approximately 7 mm in diameter. Deformation of the body 310 from the compacted state into the pre-determined shape in the expanded state may be gradual. For example, the body 310 may deform into the pre-determined shape in a progressive and incremental manner over a period of time of at least one second, or 1 to 10 seconds, or 5 to 15 seconds, or 10 to 20 seconds, or 15 to 25 seconds, or 20 to 30 seconds, or 25 to 35 seconds. Accordingly, the deformation of the body 310 may not be sudden or instantaneous, and may not be abrupt. The gradual deformation of the body 310 may prevent injury to the iris 405, 407 as the expander 300 deforms to widen the pupil 405, 407. In the expanded state, the body 310 of the expander 300 may be configured to hold apart the iris 409, 411 to maintain the enlarged pupil 405, 407 by applying a biasing force to push against the iris 409, 411.

According to various embodiments, the pre-determined physiological condition may include a pre-determined temperature. The pre-determined temperature may be a temperature of the eye anterior chamber, or any suitable temperature that may be higher than a temperature of the expander 300 in the compacted state when stored.

FIG. 3D shows a side view of the expander 300 in the expanded state of FIG. 3C. As shown, a side 320 of the body 310, in the expanded state, may be configured to engage with the iris 409, 411. Accordingly, the side 320 of the body 310 may be directly in contact with the iris 409, 411 during engagement with the iris 409, 411, and may be shaped such that the iris 409, 411 may be received by the side 320 of the body 310. Accordingly, the body 310 may include a continuous recess 322 along the circumferential surface of the body 310 with the pre-determined shape in the expanded state. The continuous recess 322 may encircle the body 110 in the expanded state. In this configuration, the iris 409, 411 may be received in the continuous recess 322.

Accordingly, with the body 110 having the continuous recess 322 in the circumferential surface of the body 310, the body 310 of the expander 300 may have a C-shaped cross-section to engage the iris 409, 411 during insertion of the expander 300 into the pupil 405, 407 of the eye 401, 403.

As proof of concept, prototypes of the expander 300 according to various embodiments were tested in enucleated porcine eyes. In the tests, shape-memory pupil expanders (with 2 proposed initial shapes, namely the M shape and the spiral shape) according to various embodiments were first inserted into the eye (maintained at a temperature of 37° C.) using a rapid prototyped injector 530 (FIG. 5) and engaged with the iris. FIG. 5 shows an illustration of inserting the expander 300 (folded in M shape 312) into the eye 401 using the injector 530. As illustrated, as the expander 300 is being inserted into the eye 401, more force may be applied via the injector 530 through the expander 300 to push the iris 409 outward slightly by 1-2 mm (indicated by arrow 532) to position the pupil expander 300 in the center of the pupil 405. After which, the injector 530 may be operated to release the expander 300. While the expander 300 is in the eye 401, the pupil expander 300 may be exposed and heated up by the temperature inside the eye 401 such that the pupil expander 300 may experience an increase of temperature from a room temperature to the temperature inside the eye 401. Upon reaching 35° C., the pupil expander 300 may be configured to expand to their pre-programmed or pre-determined shape, for example to the circular shape 316 as shown in FIG. 3B, thus resulting in enlargement of the pupil 405. FIG. 4C shows the expander 300 of FIG. 4A, originally in an M shape 312, expanded to a circular shape 316 to enlarge the pupil 409 of the eye 401. FIG. 4D shows the expander 300 of FIG. 4B, originally in a spiral shape 314, expanded to a circular shape 316 to enlarge the pupil 411 of the eye 403. Accordingly, the pupil expander 300 according to various embodiments may directly react to body temperature for deployment into the eye to enlarge the pupil. Further, no additional internal/external actuations may be required to operate the pupil expander 300 according to various embodiments thus the risks of iris damage/tearing may be minimized with the pupil expander 300 according to various embodiments.

According to various embodiments, at body temperature or a pre-determined temperature, the shape-memory pupil expanders of the various embodiments may transform into their pre-programmed or pre-determined shapes. To prevent the pupil expander from transforming too early during insertion, the injector 530 may include a holder 534 having two rod-like structures 536 that may prevent changes in shape of the pupil expander until the pupil expander has been properly positioned within the eye. Retraction of the holder 534 of the injector 530 may then allow for a slow and uniform transformation or deformation of the pupil expander for a slow and uniform expansion of the iris within 5-10 seconds. Accordingly, the pupil expander in the compacted state may be configured to engage the holder 534 of the injector 530. For example, a portion of the side of the body of the expander, in the compacted state, may be configured to engage the rod-like structures 536 of the holder 534 of the injector 530. Accordingly, the rod-like structures 536 of the holder 534 of the injector 530 may engage with a portion of the continuous recess 322 of the body 310 of the expander 300 in the compacted state for holding the expander 300 on the holder 534 of the injector 530.

Figures 6A, 6B:
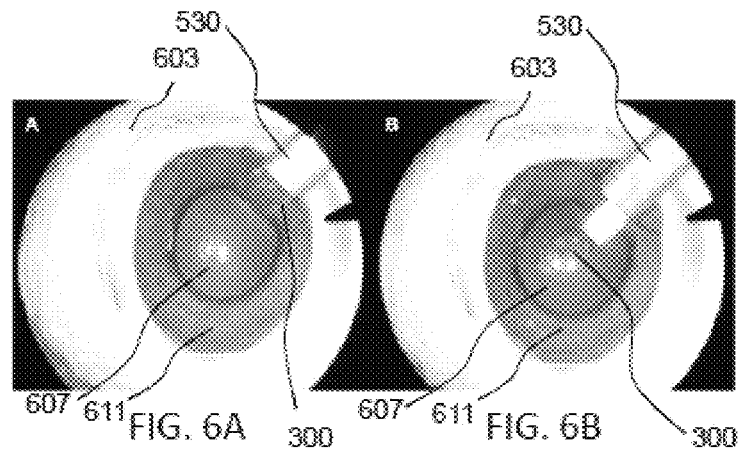
FIGS. 6A and 6B show the expander of FIG. 3 being inserted into the center of a pupil of an eye using an injector according to various embodiments.
Figures 7A, 7B, 7C, 7D:
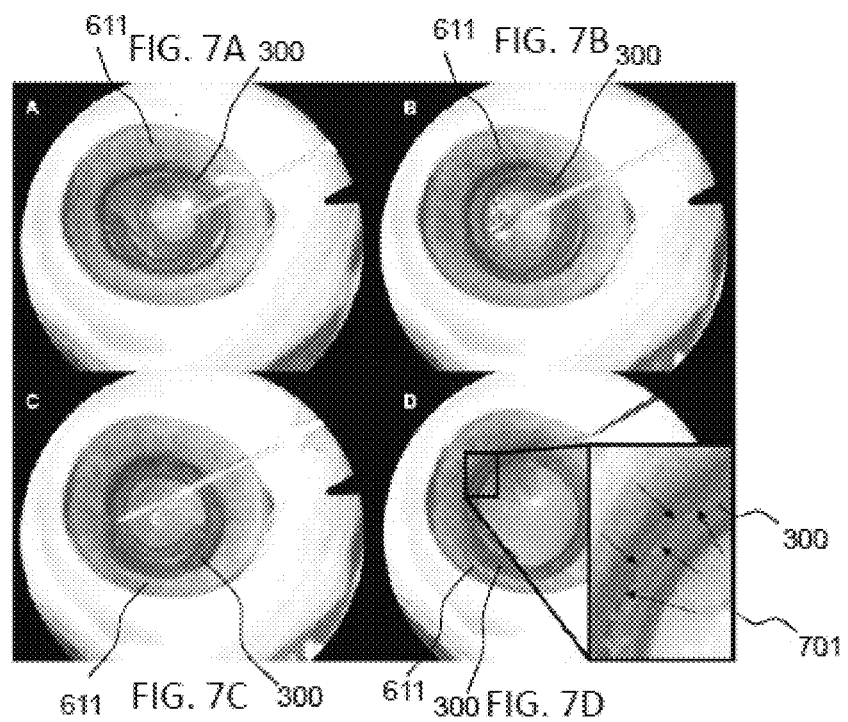
FIGS. 7A to 7D illustrate the expansion of the expander of FIG. 3 to engage the iris of an eye according to various embodiments.

FIGS. 6A, 6B, 7A to 7D illustrate a method of enlarging a pupil 607 using the pupil expander 300, which is in a spiral shape in the compacted state. According to various embodiments, a single incision of approximately 2 mm may be made on the cornea of an eye 603. A highly viscous fluid known as 'viscoelastic' may be injected into the eye 603, as per the standard practice in cataract surgery, to maintain the mechanical integrity of the anterior chamber of the eye 603. FIGS. 6A and 6B show the pupil expander 300 being inserted into the center of the pupil 607 of the eye 603 using a custom-made injector 530, having a width of approximately 2 mm and thickness of approximately 1 mm, through the single 2 mm by 1 mm incision. As shown, the pupil expander 300 may be inserted into the center of the pupil 607 without damaging the iris 611 of the eye 603. Referring to FIG. 6B, the compressed folded shape of the pupil expander 300 in the compacted state may be placed within the pupil 607 of the eye 603. As can be seen, the pupil expander 300 may fit extremely small pupil size. While the pupil expander 300 remains within the pupil 607 of the eye 603, the pupil expander 300 may be exposed to the temperature of the eye 603 such that the pupil expander 300 may experience an increase in temperature from room temperature to the temperature of the eye 603. In response to the increase in temperature due to the exposure of the pupil expander 300 to the temperature of the eye 603, the pupil expander 300 may deform gradually into a pre-determined shape in the expanded state. FIGS. 7A to 7D, illustrate the expansion of the pupil expander 300 to engage the iris 611 of the eye 603. As shown, the pupil expander 300 may gradually expand and uncoil to engage the iris 611. The deformation of the pupil expander 300 from the compacted state to the pre-determined circular shape in the expanded state may take approximately 30 seconds. The enlarged view 701 in FIG. 7D shows that the C-shaped or U-shaped cross section of the pupil expander 300 engage nicely with the iris 611.

FIGS. 8A to 8D, illustrate the expansion of the pupil expander 300 to engage the iris 811 of the eye 803 which has a pupil 807 of a size smaller than that of the eye 603 in FIGS. 7A to 7D.

FIGS. 9A to 9D illustrate the removal of the pupil expander 300 from the eye 903. As shown in FIG. 9A, the pupil expander 300, in the expanded state, may be disengaged from the iris 911 by unhooking the pupil expander 300 upwards. Subsequently, the pupil expander 300 may be removed in a clockwise direction as shown in FIGS. 9B to 9D. It is understood that the pupil expander 300 may also be removed in a counter-clockwise direction. Due to the flexibility of the pupil expander 300 in the expanded state, the pupil expander 300 may be easily removed from the eye 903 in the manner as shown in FIGS. 9A to 9D without damaging the iris 911.

According to various embodiments, the body of the pupil expander, in the expanded state, may be configured to be elastically deformable under an applied force for bending the body, and may be configured to return to the pre-determined shape upon the removal of the applied force. Accordingly, in the expanded state, although the pupil expander may have a natural tendency to maintain the pre-determined shape, the pupil expander may still be bent or deformed with standard surgical tools such that the pupil expander may be easily removed from the eye.

Various embodiments have provided a novel and elegant solution that may eliminate problems associated with the existing devices and methods for pupil expansion. Various embodiments may involve the use of a 'smart' material such as a shape-memory polymer. Such 'smart' material may be folded in the compacted state due to its high flexibility for easy insertion into the eye. To expand the pupil, various embodiments of the shape-memory pupil expander may deform to a pre-programmed or pre-determined shape, such as a circular ring, in the expanded state upon exposure to a pre-set temperature, for example as that of the eye anterior chamber, or any suitable temperature that may be higher than a temperature of the expander in the compacted state when stored.

Due to the compactness of the folded shape of the pupil expander in the compacted state according to various embodiments, the pupil expander may be inserted into the eye through a single 2 by 1 mm incision. In contrast, current devices require multiple incisions for proper use and insertion. Further, the incision required for the pupil expander according to various embodiments may also be easily smaller than the current incisions used for cataract surgery involving current devices. Various embodiments may also engage the iris along its entire circumference, while current devices may only have 4 or fewer points of contact, resulting in unwanted stress concentration that could lead to iris damage. When expanded, various embodiments may provide a large circular opening, while conventional devices may distort the iris in an unnatural manner and the opening may often remain questionable. Finally, due to its simplicity, various embodiments may be produced at an extremely low cost as a disposable expander.

Various embodiments may involve the use of a smart material, such as a shape-memory polymer, that reacts to body temperature. Accordingly, gradual pupil enlargement (within 5-10 sec) in response to body temperature may be achieved. Advantageously, no external/internal mechanical actuation may be required, thus reducing the mechanical manipulations by surgeons and risks of iris damage. As mentioned before, the use of the smart material may also allow insertion through a single incision.

Further, various embodiments may allow uniform expansion to a circular pre-programmed shape and may have a C-shaped cross-section. Advantageously, uniform stress may be applied to the entire iris circumference to reduce micro-tears/iris chafing.

Accordingly, various embodiments have provided an expander that may address the issue of insufficient pupil expansion (typically 2-3 mm) of the existing devices, the excessive iris damage such as micro-tears, chafing, high levels of strain and stress due to uneven radial expansion of the existing devices, and the multiple incisions requirement of the existing devices.

According to various embodiments, the expander may be inserted easily and may give better atraumatic pupil dilation than other expanders. Accordingly, various embodiments may have a unique and expanded use, which may revolutionize the traditional workflow for cataract surgery. Various embodiments may also be well aligned with recent innovations such as FLACS.

According to various embodiments, the expander may full engage the circumference of the iris thus minimising local stresses. The full circular iris engagement may protect the pupil margin and the iris from surgical tools during surgery.

According to various embodiments, the expander may be easily inserted and removed from the eye, thus reducing the surgery time and make it easier for the surgeon to perform the surgery.

Various embodiments may have strong potential to replace existing means of pupil expansion used today, including eye drops. Because of the large number of cataract surgeries performed worldwide (20,000,000 per year) the impact of the various embodiments may be extremely significant in terms of patient satisfaction, surgeon acceptability, and commercialization.

While the invention has been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. An expander for widening and holding apart an opening of a tissue, the expander comprising a body configured to deform from a compacted state into a pre-determined shape in an expanded state in response to a pre-determined physiological condition the body is exposed to,
   wherein the body with the pre-determined shape in the expanded state is configured to hold apart the opening of the tissue,
   wherein the body, in the compacted state, is in a folded shape, wherein the folded shape comprises a spiral shape or a coiled shape,
   wherein the pre-determined shape in the expanded state comprises an annular circular shape with a broken connection, an annular oval shape with a broken connection, an annular elliptical shape with a broken connection, or a horseshoe shape,
   wherein the body, in the expanded state, comprises a continuous recess along a circumferential surface of the body to engage the tissue, wherein the continuous recess encircles the body,
   wherein the expander further comprises a pouch enclosing the body to maintain the body in the compacted state, or the body further comprises a glue or a coating configured to maintain the body in the compacted state, and wherein the pouch or the glue is configured to be dissolvable in the tissue to expose the body for deforming from the compacted state to the pre-determined shape in the expanded state.

2. The expander as claimed in claim 1, wherein deformation of the body is gradual over a period of time of at least one second, or 1 to 10 seconds, or 5 to 15 seconds, or 10 to 20 seconds, or 15 to 25 seconds, or 20 to 30 seconds, or 25 to 35 seconds.

3. The expander as claimed in claim 1, wherein deformation of the body from the compacted state into the pre-determined shape in the expanded state causes the widening of the opening of the tissue.

4. The expander as claimed in claim 1, wherein the folded shape comprises a compressed folded shape.

5. The expander as claimed in claim 1, wherein the body, in the expanded state, is configured to be elastically deformable under an applied force for bending the body, and configured to return to the pre-determined shape upon the removal of the applied force.

6. The expander as claimed in claim 1, wherein the pre-determined physiological condition comprises a temperature, a pressure, or a concentration.

7. The expander as claimed in claim 1, wherein the physiological condition comprises a pre-determined temperature.

8. The expander as claimed in claim 1, wherein the body is further configured to deform from the compacted state into the pre-determined shape in the expanded state in response to an external stimulation.

9. The expander as claimed in claim 8, wherein the external stimulation comprises a thermal source external to the tissue, or a fluid with a pre-determined temperature.

10. The expander as claimed in claim 1, wherein a portion of the circumferential surface of the body, in the compacted state, is configured to engage a holder of an injector.

11. The expander as claimed in claim 10, wherein the holder comprises a pair of rod-like structures.

12. The expander as claimed in claim 1, wherein the body comprises a C-shaped cross section, a U-shaped cross section or a horseshoe-shaped cross section.

13. The expander as claimed in claim 1, wherein the body of the expander, in the expanded state, is configured to hold apart an iris to maintain an enlarged pupil.

* * * * *